United States Patent [19]

Ghosh

[11] 4,323,367
[45] Apr. 6, 1982

[54] GAS PRODUCTION BY ACCELERATED IN SITU BIOLEACHING OF LANDFILLS

[75] Inventor: Sambhunath Ghosh, Homewood, Ill.

[73] Assignee: Institute of Gas Technology, Chicago, Ill.

[21] Appl. No.: 161,922

[22] Filed: Jun. 23, 1980

[51] Int. Cl.$^3$ .......................... C02F 11/04; C12P 5/02
[52] U.S. Cl. .................................. 48/197 A; 48/209;
 210/603; 210/747; 210/901; 210/926; 405/129;
 435/167
[58] Field of Search ............. 48/192 A, 209; 435/167;
 210/603, 613, 747, 901, 926; 405/129

[56] References Cited

U.S. PATENT DOCUMENTS

| | | | |
|---|---|---|---|
| 1,286,017 | 11/1918 | Jones | 210/926 |
| 2,572,767 | 10/1951 | Schlenz | 210/603 |
| 3,705,851 | 12/1972 | Brauer | 210/747 |
| 3,732,697 | 5/1973 | Dickson | 405/129 |
| 3,846,292 | 11/1974 | Lecompte | 210/926 |
| 4,022,665 | 5/1977 | Ghosh et al. | 435/140 |

OTHER PUBLICATIONS

"Methane Production, Recovery, and Utilization from Landfills", James et al., Symposium Papers on Energy from Biomass and Wastes, Wash., D.C., Aug. 1978, pp. 317-324.
"Recovery and Utilization of Methane Gas from a Sanitary Landfill . . . ", Stearns et al., Symposium Papers on Energy from Biomass and Wastes, Wash., D.C., Aug. 1978, pp. 325-343.
Anaerobic Digestion, I. The Microbiology of Anaerobic Digestion, Toerien et al., Water Research, vol. 3, pp. 385-416, Pergamen Press (1969).

Primary Examiner—Peter F. Kratz
Attorney, Agent, or Firm—Thomas W. Speckman

[57] ABSTRACT

A process for improved gas production and accelerated stabilization of landfills by accelerated in situ bioleaching of organic wastes by acid forming bacteria in substantially sealed landfills, passing the leachate of hydrolysis and liquefaction products of microbial action of the microorganisms with the organic material to an acid phase digester to regenerate the activated culture of acid forming microorganisms for recirculation to the landfill, passing the supernatant from the acid phase digester to a methane phase digester operated under conditions to produce methane rich gas. The supernatant from the methane phase digester containing nutrients for the acid forming microorganisms and added sewage sludge or other desired nutrient materials are circulated through the landfill. Low Btu gas is withdrawn from the acid phase digester while high Btu gas is withdrawn from the methane phase digester and may be upgraded for use as SNG. The process of this invention is applicable to small as well as large organic waste landfills, provides simultaneous disposal of municipal solid waste and sewage sludge or other aqueous organic waste in a landfill which may be stabilized much more quickly than an uncontrolled landfill as presently utilized.

12 Claims, 5 Drawing Figures

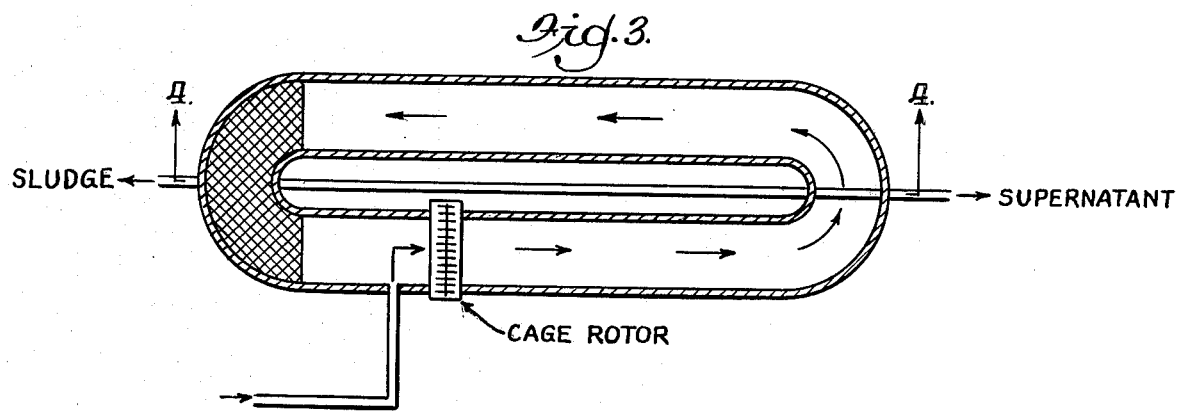
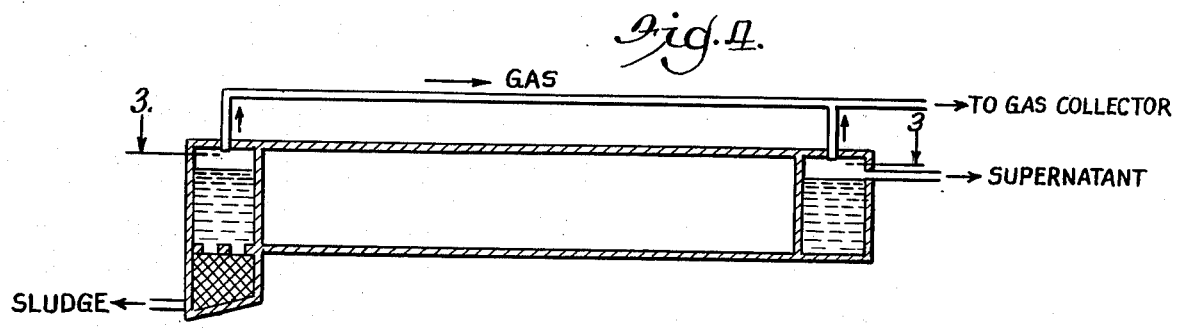
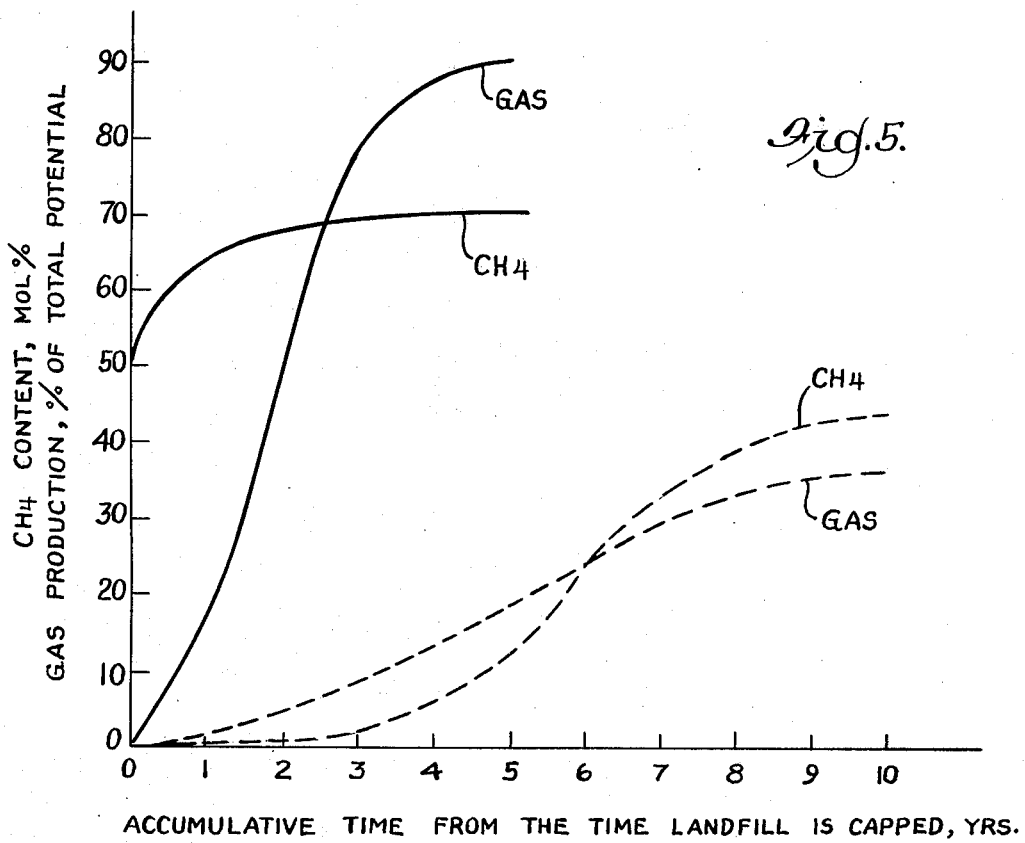

GAS PRODUCTION BY ACCELERATED IN SITU BIOLEACHING OF LANDFILLS

BACKGROUND OF THE INVENTION

1. Field of the Invention

This invention relates to improved production of gas, particularly methane, from sanitary landfills or other confined deposits of organic matter.

2. Prior Art

Sanitary landfills formed by filling a land area with successive layers of solid waste, principally household waste, and layers of earth or soil are well known. The uncontrolled landfill depends upon natural biological action, precipitation and climate to effect decomposition. In areas where oxygen is present, the decomposition will be aerobic and in areas where little oxygen is present, such as at the deeper depths, decomposition will be slower and anaerobic producing methane containing gas. Initially, there is no methane production from the landfill and it increases very slowly with time to an amount representing only about 15 to 20 percent of the total potential production after many years. The formed methane is an explosion or fire hazard and may migrate to buildings or structures several hundred feet from the landfill if not removed from the landfill. Further, the natural precipitation draining out of the landfill may carry highly toxic contaminated water to contaminate underground water supplies, surface streams and wells. Due to the very slow stabilization, the uncontrolled landfill is not usable for other purposes for long periods of time and thus, particularly near metropolitan areas, represents a large waste of land resources.

One approach to rendering waste disposal landfills safer is suggested by U.S. Pat. No. 3,586,624 which teaches a liquid impervious containment of the lower portion of the landfill with continuous flow of water through the landfill to accelerate the decomposition, decrease the fire hazard and flush contaminants from the landfill in a controlled manner. The water drained from the landfill may be treated for removal of contaminants and recycled to the landfill.

In the past, methane gas has been frequently vented and flared from landfills as a safety precaution. However, in recent years and especially in view of energy conservation, the recovery and utilization of methane from sanitary landfills and desirability of early utilization of the landfill area for other purposes has been recognized. "Methane Production, Recovery, and Utilization from Landfills", James, S. C. and Rhyne, C. W., Symposium Papers on Energy from Biomass and Wastes, Washington, D. C., Aug. 14–18, 1978, pgs. 317–324, and "Recovery and Utilization of Methane Gas from a Sanitary Landfill—City of Industry, California", Stearns, R. P., Wright, T. D. and Brecher, M., Symposium Papers on Energy from Biomass and Wastes, Washington, D. C., Aug. 14–18, 1978, pgs. 325–343. Presently methane is most frequently recovered from landfills by pipes extending into the landfill and transporting the methane containing gas formed within the landfill to a collecting area for further treatment.

In the United States, about 1151 million tons (dry) of organic wastes are generated annually in the form of municipal solid waste, agricultural residue, manure, logging and wood manufacturing residues, municipal sludge solids, industrial organic wastes and miscellaneous organic wastes representing production potential of 11.8 trillion SCF/yr. of substitute natural gas (SNG). The most readily available solid waste for energy recovery is municipal solid waste estimated to be currently generated at about 260 million tons per year in the United States. Additionally, urban areas in the United States produce about 25 million tons (dry) per year of organic waste solids in sewage sludge. These wastes have presented intractable waste management and disposal problems and represent continuing loss of energy resources.

SUMMARY OF THE INVENTION

This invention relates to a process for improved gas production providing higher gas production rates and yields by accelerated in situ bioleaching of organic wastes in substantially sealed landfills. Methane producing anaerobic digestion systems utilize acid forming bacteria and methane producing organisms as are well known to be employed to produce methane from sewage sludge and are suitable for use in the process of this invention. Two phase digestion is used under controlled digester conditions in the process of this invention, that is, acid phase digestion operated at mesophilic or thermophilic conditions to promote the growth of the acid forming bacteria and a second methane phase digestion operated at mesophilic or thermophilic conditions to promote the growth of the methane producing organisms. In the process of this invention organic material in a substantially sealed landfill is contacted in situ with an aqueous activated culture of hydrolytic and liquefying anaerobic microorganisms under growth conditions to produce a bioleachate of hydrolysis and liquefaction products of microbial action of the microorganisms with the organic material. The bioleachate and the deactivated acid forming bacteria are passed from the landfill to an acid phase digester to regenerate the activated culture of hydrolytic and liquefying anaerobic microorganisms for recirculation to the landfill. The supernatant from the acid phase digester is passed to the methane phase digester operated under conditions to produce gas rich in methane. The supernatant from the methane phase digester, containing nutrients for the acid forming microorganisms, is mixed with the activated culture of hydrolytic and liquefying anaerobic microorganisms from the acid phase digester and recirculated to contacting organic material in situ in the substantially sealed landfill. Low Btu gas is withdrawn from the acid phase digester and may be also withdrawn from the landfill from time to time while high Btu gas is withdrawn from the methane phase digester for direct use or upgrading for use as substitute natural gas (SNG). Sewage sludge or other organic waste materials may be added to the landfill to increase the biological activity in the landfill, improve the nutrient balance and to dispose of the organic waste.

The process of this invention provides rapid onset of landfill bioconversion, increased gas production rate and higher concentrations of methane resulting in stabilized landfill available for other use much sooner than conventional landfills. In conventional landfills, biological gasification is severely retarded and there is a long time lag between closing of the landfill and onset of active methane fermentation, which then continues at very slow rates and in uncontrolled manners for many years. Further, the methane gas formed in the landfill migrates both vertically and laterally in an uncontrolled fashion causing a very hazardous situation. The process of this invention greatly decreases the formation of methane in the landfill itself, and enhances overall energy production from the landfill by operation of two phase digestion under controlled conditions.

It is an object of this invention to provide a process for improved gas production from landfills of solid organic wastes.

It is another object of this invention to reduce fire and explosion hazards and pollution of areas surrounding solid organic waste landfills.

It is still another object of this invention to increase the methane content of gaseous products produced by anaerobic digestion based upon solid organic waste landfills.

It is yet another object of this invention to provide a process which is suitable for a wide variety of sizes of landfills, applicable to small as well as large organic waste landfills.

It is still another object of this invention to provide simultaneous disposal of municipal solid waste and sewage sludge or other aqueous organic waste in a substantially sealed landfill.

BRIEF DESCRIPTION OF THE DRAWINGS

These and other objects, advantages and features of this invention will be apparent from the description together with the drawings wherein:

FIG. 3 is a top sectional view of one preferred anaerobic digester configuration for use in the process of this invention;

FIG. 4 is a side sectional view through the anaerobic digester shown in FIG. 3; and FIG. 5 is a graph showing calculated gas production from a landfill according to the process of this invention compared with gas production from conventional landfills.

DESCRIPTION OF THE PREFERRED EMBODIMENTS

The process of this invention is applicable to landfills of all types of organic wastes. By the term "organic waste" as used in this disclosure and the appended claims, I mean all types of organic refuse including sewage sludge, animal waste, municipal waste, industrial waste, forestry waste, agricultural waste, and the like. By forestry waste and agricultural waste I mean to include portions of plants after some physical or chemical treatment, usually not including the entire plant, for example, stumps from logging, sawdust, wood chips, corn stalks, corncobs and bagasse.

Municipal solid waste landfills constitute an important application of the process of this invention. Treatment of municipal solid waste and industrial solid waste for removal of undesired material such as glass, metals, plastics, stones, and the like, is well known to the art. Municipal solid waste contains over 50 weight percent (dry) cellulosics. Exemplary average composition of raw municipal solid waste is shown in Table I for municipal solid waste collected in Indianapolis, Ind.

TABLE I

| Components | Weight % dry |
| --- | --- |
| Paper Products | 45.7 |

TABLE I-continued

| Components | Weight % dry |
| --- | --- |
| Wood | 2.1 |
| Textiles and Rags | 1.9 |
| Food and Garden Wastes | 10.9 |
| Total Cellulosics | 60.6 |
| Metallics | 13.6 |
| Glass, Ceramics, etc. | 16.6 |
| Dirt, Ash, Rocks | 3.0 |
| Plastics | 2.1 |
| Bulky Materials | 3.0 |
| Rubber and Leather | 1.1 |
| Total Non-Cellulosics | 39.4 |

The municipal solid waste is preferably shredded followed by magnetic separation of ferrous metals to reduce landfill volume and permit recovery of the ferrous metal. It is also preferred to separate glass from the waste also to reduce landfill volume and provide recovery for recycling.

Figure 1:
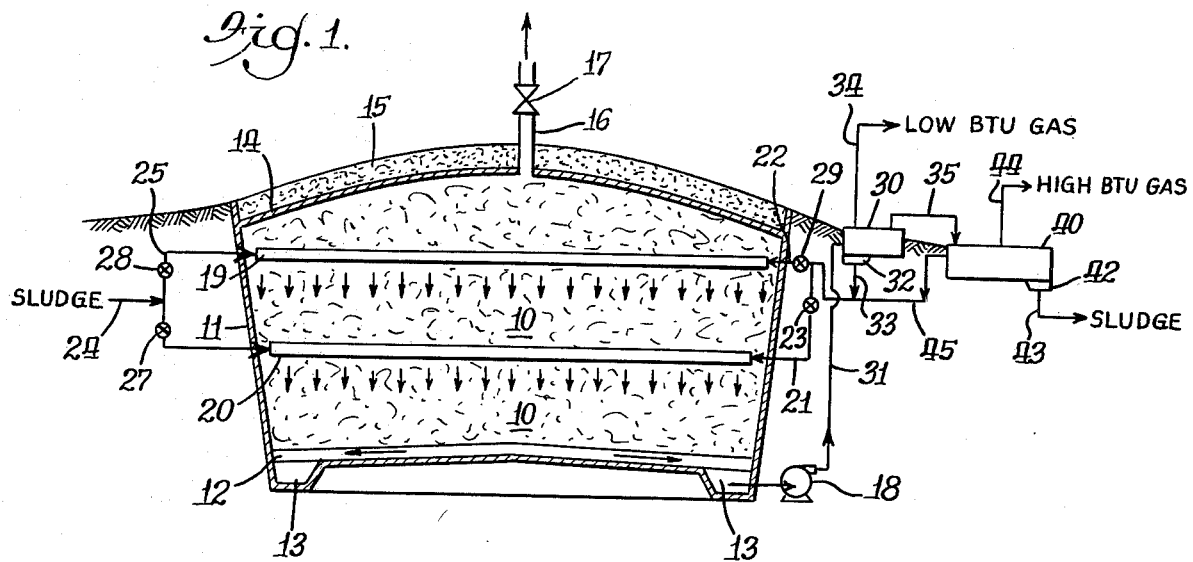
FIG. 1 is a sectional schematic view of a landfill cell and gas production digesters according to this invention.

The landfill area to be filled with organic waste is isolated from ground water and surrounding soil formations using a linear having sides and a floor shown as 11 in FIG. 1. The liner may be any suitable barrier such as compacted clay, asphalt or other commercially available liner materials. The floor has collection drain 12 leading to sump 13 for recovery of the liquid leachate. The organic waste is spread and compacted in layers, 6 to 8 foot lifts, by conventional methods of constructing sanitary landfills. Collection drain 12 is preferably surrounded with crushed stone to enhance the liquid flow to the collection drain. During filling of the landfill with organic waste 10, liquid distribution means, shown in FIG. 1 as pipes 20 and 19, are put into place to assure distribution of liquid throughout the landfill volume. The liquid distribution means may include any arrangement of pipes or conduits with suitable holes or other means for distributing liquid, including liquid-solid slurries, both horizontally and vertically throughout the landfill volume. When the landfill is full of organic waste, top liner 14 and compact soil 15 is put into place to substantially seal the landfill. Gas withdrawal pipe 16 having valve 17 is provided to withdraw any low Btu gas collecting at the top of the landfill.

Bioconversion of the organic waste is achieved by contacting the organic waste with an aqueous activated culture of hydrolytic and liquefying anaerobic microorganisms under growth conditions to produce a bioleachate of hydrolysis and liquefaction products of microbial action of the microorganisms with the organic waste material in situ. The active culture also contains desired nutrients for the hydrolytic and liquefying anaerobic microorganisms and by continued application of the activated microorganisms, moisture and nutrients, the landfill is transformed into a medium supporting the growth of the hydrolytic and liquefying microorganisms. Growth and continued supply of the acid forming microorganisms may be enhanced by also supplying to the landfill aqueous liquid organic waste such as sewage sludge.

Any active methane producing mesophilic or thermophilic anaerobic digestion system may be used in the process of this invention. Methane-producing anaerobic systems utilizing acid forming bacteria and methane-producing organisms as are well known to be employed to produce methane from sewage sludge can be employed in practice of the present invention. A review of the microbiology of anaerobic digestion is set forth in Anaerobic Digestion, 1. The Microbiology of Anaerobic Digestion, D. F. Toerien and W. H. J. Hattingh, Water Research, Vol. 3, pages 385–416, Pergamon Press (1969). As set forth in that review, the principal suitable acid forming bacteria include species from genera including Aerobacter, Aeromonas, Alcaligenes, Bacillus, Bacteroides, Clostridium, Escherichia, Klebsiella, Leptospira, Micrococcus, Neisseria, Paracolobactrum, Proteus, Pseudomonas, Rhodopseudomonas, Sarcina, Serratia, Streptococcus and Streptomyces. Exemplary methane-producing organisms suitable for use in the present invention include members of Methanobacterium, Methanococcus and Methanosarcina, specific members being *Methanobacterium formicicum, Methanosarcina barkerii, Methanobacterium omelianskii, Methanococcus vannielii, Methanobacterium sohngenii, Methanosarcina methanica, Methanococcus mazei, Methanobacterium suboxydans* and *Methanobacterium propionicum.* It is usually preferred to use mixed cultures to obtain the most complete fermentation action. Nutritional balance and pH adjustments may be made to the anaerobic system as is known to the art to optimize hydrolytic and liquefying action or methane production from the culture used, dependent upon the phase of the process.

The growth of the acid forming bacteria in the organic waste landfill is promoted by maintaining a low pH of the introduced culture of about 4 to 7 and high throughput rates, for example, displacement of the pore volume liquid in about 1 to 4 days. As the aqueous culture moves down through the organic waste bed, the microbial action extracts and captures the hydrolysis and liquefaction products of the organic waste to produce a bioleachate. The bioleachate and deactivated acid forming organisms may be collected by a system of riser pipes and underdrains within the landfill for passage to an acid phase digester. Thus, the principal bioactivity in the landfill is the formation of the bioleachate and not the production of methane gas. Some low Btu gas and smaller amounts of methane may be produced in the landfill volume and may be removed from time to time by gas withdrawal pipe 16, but wells as used in the past for gas recovery from landfills are not necessary nor desirable. The relatively high rates of liquid throughput in the landfill provide removal of reaction products and toxicants from the landfill.

The bioleachate and deactivated acid forming microorganisms collected in sump 13, shown in FIG. 1, are transported by pump 18 through conduit 31 to acid phase digester 30. The digestion system which serves as a generator of activated acid forming microorganisms and gasification of the bioleachate may be a conventional single stage, completely mixed digester, but is preferably a two phase digester system with a first digester operated under conditions promoting the growth of acid forming microorganisms and the second digester operated under conditions promoting the growth of methane forming microorganisms. Two phase anaerobic digestion is known to the art and is further disclosed in U.S. Pat. No. 4,022,665. The digesters shown in FIG. 1 are closed-loop plug flow digesters with built-in settling systems to facilitate the withdrawal of activated cultures, the digesters being more fully described with respect to FIGS. 3 and 4.

The acid phase digester 30 is fed the bioleachate and deactivated acid forming microorganisms through conduit 31. Anaerobic digestion is carried out in the acid phase digester under mesophilic, 15° to 45° C., or thermophilic, 45° to 70° C., temperatures and a detention time of about 1 to 3 days. Mesophilic conditions are preferred when the organic waste is municipal solid waste. The pH of the acid phase digester is maintained at about 5 to 7 and loading is maintained at about 0.4 to 2.0 lb. VS/ft$^3$-day. These conditions promote the growth of activated acid forming microorganisms. The activated hydrolytic and liquefying microorganisms are collected in digester sump 32 and pass from the digester in recirculation conduit 33. Low Btu gas, in the order of 150 to 400 Btu/SCF gas, is formed by the acid forming anaerobic culture and may be withdrawn from the acid phase digester by low Btu gas withdrawal pipe 34. Such low Btu gas may be used to supply process heat or other energy consumed in the process. The supernatant from the acid phase digester is rich in volatile fatty acids, alcohols and other solubles and is transferred to methane phase digester 40 by supernatant transfer conduit 35.

Methane phase digester 40 is operated under conditions to promote the growth and action of methane forming microorganisms. The loading is about 0.01 to 0.40 lb. VS/ft$^3$-day and the digester operated at a mesophilic or a thermophilic temperature for a detention time of about 3 to 30 days. The pH of the methane phase digester is maintained between about 6.5 and 8.0. Sludge from the methane phase digester is collected in digester sump 42 and is withdrawn through sludge conduit 43 to purge the system of inhibitory substances and toxic microbial metabolites. High Btu gas, about 500 to 800 Btu/SCF gas, is withdrawn through high Btu gas withdrawal pipe 44. The high Btu gas from methane phase digester 40 has greater than 50 mole percent methane shortly after initiation of the process and increases to 60 to 70 percent methane after a few months of operation of the landfill. The methane containing gas produced may be upgraded by methods known to the art to provide substitute natural gas (SNG). The total digester volume, acid phase and methane phase, is about 3 to 5 percent of the total volume of the landfill.

Supernatant from the methane phase reactor is rich in inorganic nutrients and organic growth factors and is withdrawn through supernatant withdrawal conduit 45 for mixing with the activated hydrolytic and liquefying microorganism culture for recirculation to the landfill. The supernatant from the methane phase digester may be passed to a mixing tank (not shown) for mixing with the activated acid forming microorganisms withdrawn from the acid phase digester for recirculation. This will provide a nutrient-rich active culture of acid forming bacteria which may be drawn upon for recirculation by recirculation conduits 21 and 22 controlled by valves 23 and 29 and necessary pumps and controls (not shown) for supplying distributor means 19 and 20, respectively, within organic waste landfill 10. Aqueous organic wastes such as sewage, industrial wastes, feed lot runoff, sewage or industrial sludge, may be added to the landfill through the distributor means. Nutrients, pH adjusting chemicals and other desired chemicals may be added in this fashion or separately. Such wastes provide nutrients for the microorganisms and accelerated bioleaching in addition to simultaneous gasification at enhanced rates. The aqueous liquids or slurries may be provided to distributor means 19 and 20 by liquid supply conduit 24 and liquid conduits 25 and 26 feeding into distributor means 19 and 20, respectively. The flow to each of the distributor means may be controlled by valves 27 and 28 and pumps and controls (not shown). It is suitable to add to a municipal solid waste landfill about ½ to 3 weight percent (dry basis) sewage sludge slurry based upon weight of municipal solid waste as received. Thus, a unified sewage sludge and municipal solid waste disposal system is advantageously obtained in a fashion interacting to promote high energy recovery.

Figure 2:
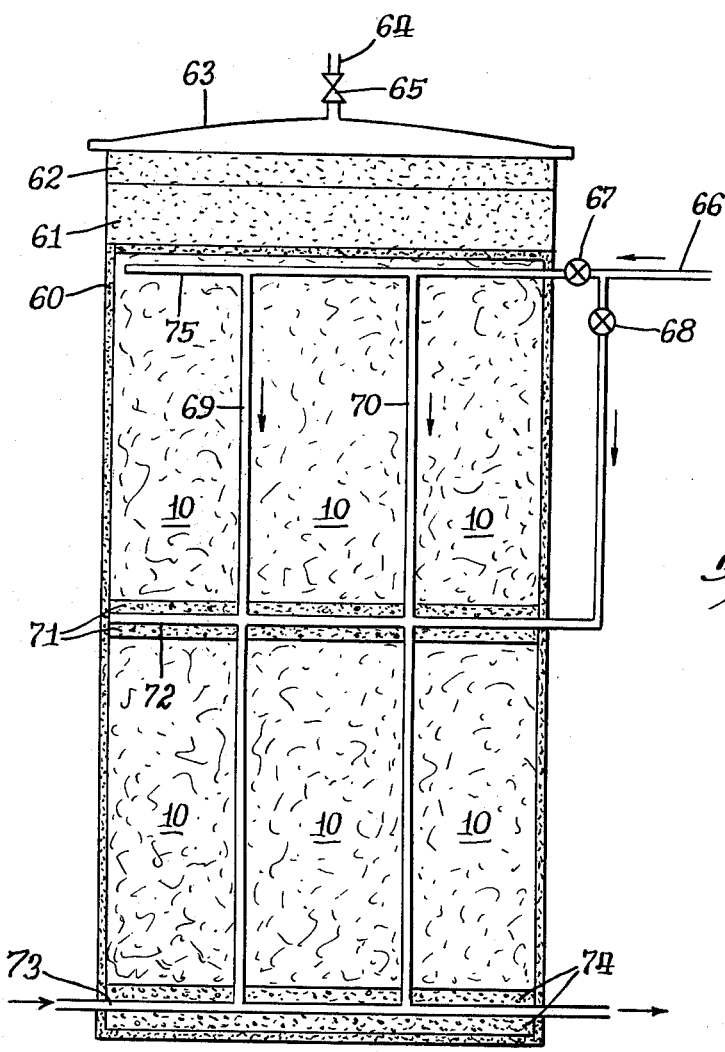
FIG. 2 is an enlarged sectional schematic view of a portion of a landfill cell.

FIG. 2 shows a sectional view through a portion of a landfill cell according to one embodiment of this invention and suitable for laboratory work. FIG. 2 shows activated acidogenic anaerobic culture and nutrient supply conduit 66 controlled by valves 67 and 68 supplying the active acidogenic culture together with nutrients and aqueous organic waste, if desired, to distributor means 75 and 72, respectively. The distributor means may be perforated pipes to allow desired distribution throughout the landfill area and may be packed with or surrounded by crushed rock or gravel. The horizontal distributor means 72 and 75 are interjoined by vertical risers 69 and 70 which are also perforated pipes which may be packed with or surrounded by crushed rock. Even distribution of the liquids throughout the landfill volume may be enhanced by utilizing different sized crushed rock or different sized perforations in the pipes. As shown in FIG. 2, risers 69 and 70 may be joined directly with underdrain 73 which is also surrounded by gravel or soil 74. Underdrain 73 collects the leachate and deactivated microorganisms from the landfill for transfer to the acid phase digester. The digester is enclosed by polyvinylchloride liner 60 and covered with clay 61 and dirt 62. Gas collection cover 63 is provided with gas withdrawal pipe 64 and valve 65.

It is seen that the application of activated acidogenic anaerobic culture on a continual basis throughout the landfill serves to moisten the landfill bed and promote active acid phase decomposition relatively uniformly throughout the landfill. Nutrients for the acid forming anaerobes may be distributed throughout the landfill bed on a continuous basis to encourage the hydrolytic and liquefying action of the acid forming organisms. Further, the removal of the microbial reaction products from the reaction zones throughout the landfill further rapid anaerobiosis and bioleaching of the organic waste in the landfill.

Any anaerobic digester and various means for increasing methane yield, gas quality and digestion kinetics such as feed pretreatment, residue post-treatment and recycling or advanced digestion modes may be used in conjunction with the process of this invention. One preferred configuration for each of the digesters in the two phase system of a preferred embodiment of this invention is shown in FIGS. 3 and 4. The digester tank 80 is in oval, or race track, form. The digester is not completely filled with liquid but always has a suitable gaseous headspace. The digester is supplied liquid by supply conduit 81 just behind cage rotor 85. Cage rotor 85 is used for propelling the liquid through the digester as well as mixing and gas transfer from the liquid to the headspace and is of a type known to the art and now commercially used in oxidation ditches. Other aids, such as baffles, may be used to enhance transfer of gases from the moving liquid. As the liquid passes around the digester tank, supernatant is removed by supernatant conduit 82 and gas from the headspace is removed by gas removal conduits 86 to gas collector conduit 87. As the liquid moves through the digester, it passes over settler section 83 which provides a sump for gravity separation of the heavy materials in the digester which may be removed by removal conduit 84. In the acid phase digester, the activated acidogenic microorganisms collect in settler section 83 while in the methane phase digester, sludge will collect in settler section 83. Suitable heaters, means for additions for pH adjustments and other anaerobic digester features known to the art may be readily adapted to this type of digester. The digester of this type is proposed for use in the process of this invention in view of its effective utilization of tank volume for steady state biological reactions with low energy requirements for mixing and gas transfer and low overall costs.

FIG. 5, by dotted lines, shows total gas production and methane production from presently used uncontrolled sanitary municipal solid waste landfill. The bioactivity in such landfills takes place as a result of natural environmental conditions and the produced gas is withdrawn from the landfill by wells distributed throughout the landfill. It is seen that for the first several years gas production is very low and only after 9 to 10 years reaches about one-third of its total potential. Likewise, the methane fraction of the gas produced is very low, reaching only 10 percent after 5 years and about 45 percent after 10 years. The solid lines show calculated gas production from municipal solid waste landfills according to the process of the present invention. It is seen that the total gas production increases rapidly a short time after the landfill is capped, reaching over 50 percent of its total potential within 2 years and up to about 90 percent of its total potential in about 5 years. Likewise, the concentration of methane in the produced gas is in excess of 50 mole percent initially and increases to about 70 percent within the first 3 to 4 years following closing of the landfill. Practice of the process of this invention, therefore, provides a stabilized landfill which may be used for other purposes in a fraction of the time that landfills are being returned to other uses when present uncontrolled landfill practices are used.

EXAMPLE I

A landfill cell as shown in FIG. 2 is constructed from polypropylene or polyethylene tanks about 6 feet tall and 3½ feet in diameter to provide 50 ft$^3$ landfill capacity. Coarse-shredded and magnetically separated municipal solid waste having an analysis as set forth above for Indianapolis municipal solid waste is placed in the cell in lifts of 3 feet and compacted to produce a bulk density of 20 lbs./ft$^3$, or a total of 1000 lbs. The bottom 3 feet of waste is covered with 3 inches of soil and the top portion of waste put in place. The top of the waste is covered with a polyvinylchloride cap which is covered with 6 inches of compacted montmorillonite clay and 3 inches of dirt. An acid phase digester and a methane phase digester of the configuration shown in FIGS. 3 and 4 are connected to each other and to the landfill cell in the manner shown in FIG. 1. The acid phase digester is sized to accommodate an active culture volume of 10 liters and the methane phase digester sized to accommodate an active culture volume of 40 liters. An active anaerobic culture of acid forming microorganisms from an existing culture is transferred to the acid phase digester and an active anaerobic culture of methane forming microorganisms from an existing culture is transferred to the methane phase digester. Pumping of liquid from the digesters through the distribution pipes in the landfill is started and continued at the rate of 1 l/day from the settler portion of the acid phase digester which is rich in activated hydrolytic and liquefying microorganisms; 3 l/day supernatant from the methane phase digester which is rich in nutrients for the microorganisms; and 0.25 l/day added liquid which may be aqueous organic waste or other nutrients or materials for the system adjustment or balance. Thus, about 4.25 l/day bioleachate is collected from the landfill and passed to the acid phase digester. Supernatant in an amount of 3.25 l/day is transferred from the acid phase to the methane phase digester making a detention time of 2.3 days in the acid phase digester which is maintained at 35° C. and pH of 6. The methane phase digester is maintained at 35° C. and a pH of 7.5 with 3 l/day supernatant withdrawn for recycle to the landfill and 0.25 l/day withdrawn as sludge making a detention time of 12.3 days. The landfill cell is stabilized after 5 months of continuous operation with 400 ft$^3$ low Btu gas (30% by volume methane) being withdrawn from the acid phase digester and 2100 ft$^3$ high Btu gas (70% by volume methane) being withdrawn from the methane phase digester.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A process for improved gas production by accelerated in situ bioleaching of organic waste landfills comprising:

contacting said organic waste in a substantially sealed landfill in situ with an aqueous activated culture of hydrolytic and liquefying anaerobic microorganisms under growth conditions to produce a bioleachate of hydrolysis and liquefaction products of microbial action of said microorganisms with said organic waste and to produce deactivated hydrolytic and liquefying anaerobic microorganisms;

passing said bioleachate and deactivated microorganisms from said landfill to an acid phase digester operated at mesophilic or thermophilic conditions to regenerate said activated culture of hydrolytic and liquefying anaerobic microorganisms;

passing the supernatant from said acid phase digester to a methane phase digester operated at mesophilic or thermophilic conditions to produce gas rich in methane;

recirculating a mixture of said activated culture of hydrolytic and liquefying anaerobic microorganisms from said acid phase digester and the supernatant from said methane phase digester to contacting organic waste in situ in said substantially sealed landfill; and withdrawing low Btu gas from said acid phase digester and high Btu gas from said methane phase digester.

2. The process of claim 1 wherein said acid phase digester is operated at a pH of about 5 to 7 with loading of about 0.4 to 2.0 lb. VS/ft$^3$-day for detention time of about 1 to 3 days and said methane phase digester is operated at a pH of about 6.5 to 8.0 with loading of about 0.01 to 0.40 lb. VS/ft$^3$-day for detention time of about 3 to 30 days.

3. The process of claim 1 wherein said aqueous activated culture of hydrolytic and liquefying anaerobic microorganisms introduced to said landfill has a pH of about 4 to 7.

4. The process of claim 1 wherein the volume of said aqueous activated culture of hydrolytic and liquefying anaerobic microorganisms and added liquid nutrient displaces the pore volume liquid in said landfill in about 1 to 4 days.

5. The process of claim 1 wherein said aqueous activated culture of hydrolytic and liquefying anaerobic microorganisms is distributed throughout said landfill by horizontal and vertical porous pipes.

6. The process of claim 1 wherein said organic waste landfill comprises municipal solid waste.

7. The process of claim 6 wherein said digesters are operated under mesophilic conditions.

8. The process of claim 1 wherein liquid sewage sludge is mixed with said aqueous activated culture of hydrolytic and liquefying microorganisms.

9. The process of claim 1 wherein about ½ to 3 weight percent liquid sewage sludge, dry basis, based upon weight of municipal solid waste as received is added to a municipal solid waste landfill.

10. The process of claim 1 wherein low Btu gas, about 150 to 400 Btu/SCF, is withdrawn from said acid phase digester.

11. The process of claim 1 wherein high Btu gas, about 500 to 800 Btu/SCF, is withdrawn from said methane phase digester.

12. The process of claim 1 wherein said digesters are closed oval tubes wherein liquid is supplied to partially fill the digester, passed through a liquid-gas mixing means, passed through a digesting phase, through a settler section wherein heavy portions are separated by gravity and removed from the digester, and gas is removed from the headspace and supernatant from the liquid volume.

* * * * *